United States Patent
Whitney et al.

(10) Patent No.: US 9,904,075 B2
(45) Date of Patent: Feb. 27, 2018

(54) HIGH-VOLTAGE H-BRIDGE CONTROL CIRCUIT FOR A LENS DRIVER OF AN ELECTRONIC OPHTHALMIC LENS

(71) Applicant: Johnson & Johnson Vision Care, Inc., Jacksonville, FL (US)

(72) Inventors: Donald Whitney, Melbourne, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 14/977,736

(22) Filed: Dec. 22, 2015

(65) Prior Publication Data

US 2017/0176773 A1    Jun. 22, 2017

(51) Int. Cl.
*G02C 7/00* (2006.01)
*G02C 7/04* (2006.01)
(Continued)

(52) U.S. Cl.
CPC ............ *G02C 7/083* (2013.01); *A61F 2/1635* (2013.01); *G02C 7/04* (2013.01); *G02C 7/085* (2013.01);
(Continued)

(58) Field of Classification Search
CPC . G02C 7/022; G02C 7/02; G02C 7/04; G02C 7/027; G02C 2202/16; G02C 2202/22; G02C 7/06; G02C 7/028; G02C 7/049; G02C 2202/20; G02C 7/024; G02C 7/061; G02C 7/083; G02C 11/10; G02C 7/041; G02C 7/08; G02C 7/101; G02C 7/104
(Continued)

(56) References Cited

U.S. PATENT DOCUMENTS 6,111,769 A    8/2000  Zhang et al.
9,351,827 B2 *  5/2016  Toner ................ G02C 7/04
(Continued)

FOREIGN PATENT DOCUMENTS

EP       2648031 A1   10/2013
WO  WO2002011288 A2    2/2002
WO  WO 2011163080 A1 * 12/2011  ........... A61F 2/1624

OTHER PUBLICATIONS

WO 2011163080 A1.*

(Continued)

*Primary Examiner* — Thomas K Pham
*Assistant Examiner* — Sharrief Broome

(57) ABSTRACT

A lens driver or lens driver circuitry for an ophthalmic apparatus comprising an electronic system which actuates a variable-focus optic is disclosed herein. The lens driver is part of an electronic system incorporated into the ophthalmic apparatus. The electronic system includes one or more batteries or other power sources, power management circuitry, one or more sensors, clock generation circuitry, control algorithms and circuitry, and lens driver circuitry. The lens driver circuitry includes one or more power sources, one or more high voltage generators and one or more switching circuits. Specifically, the lens driver comprises an H-bridge/H-bridge controller for providing the proper voltage, including polarity, to drive the electronic included in the ophthalmic apparatus.

30 Claims, 10 Drawing Sheets

(51) Int. Cl.
*G02C 7/02* (2006.01)
*G02C 7/08* (2006.01)
*G02C 7/10* (2006.01)
*G02C 7/12* (2006.01)
*H02M 3/158* (2006.01)
*A61F 2/16* (2006.01)
*A61F 2/48* (2006.01)

(52) U.S. Cl.
CPC ............... *G02C 7/101* (2013.01); *G02C 7/12* (2013.01); *H02M 3/158* (2013.01); *A61F 2002/482* (2013.01)

(58) Field of Classification Search
USPC ........... 351/159.01, 159.02, 159.031, 159.39
See application file for complete search history.

(56) References Cited

U.S. PATENT DOCUMENTS

| | | | | |
|---|---|---|---|---|
| 2004/0095119 A1* | 5/2004 | Kernahan | ............. | H02M 3/157 323/282 |
| 2009/0021175 A1 | 1/2009 | Wendt et al. | | |
| 2011/0188115 A1* | 8/2011 | Sharp | ............... | B29D 11/00644 359/465 |
| 2013/0258275 A1 | 10/2013 | Toner et al. | | |
| 2013/0261743 A1 | 10/2013 | Humphreys et al. | | |
| 2014/0184278 A1 | 7/2014 | Zeng | | |
| 2015/0229207 A1 | 8/2015 | Kim | | |

OTHER PUBLICATIONS

Zhang et al., A Capacitive-loaded Level Shift Circuit for Improving the Noise Immunity of High Voltage Gate Drive IC. Proceedings of the 27th International Symposium on Power Semiconductor Devices & IC's, May 14, 2015, pp. 173-176 Whole document, especially Figures 1-2.

Xiang et al., Gate Drive Circuit for H-Bridge High-Side Power MOSFETs with High Voltage Level Shifter. Microelectronics, Apr. 30, 2011, vol. 41, No. 2, pp. 207-210 Whole document, especially Figures 1-2.

H-Bridge Drivers. Nov. 29, 2014 https://web.archive.org/web/20141129020316/http:/www.modularcircuits.com/b log/articles/h-bridge-secrets/h-bridge_drivers/.

IPOS Singapore Search Report Application No. 10201610452R Date of Completion of Search Sep. 28, 2017.

* cited by examiner

HIGH-VOLTAGE H-BRIDGE CONTROL CIRCUIT FOR A LENS DRIVER OF AN ELECTRONIC OPHTHALMIC LENS

BACKGROUND OF THE INVENTION

1. Field of the Invention

The present invention relates to electronic circuits for powering a variable-optic electronic ophthalmic lens or other similar device, and more particularly, to H-Bridge type switching circuits for a lens driver configured to control optic elements in a variable-optic electronic ophthalmic lens.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the pre-corneal (tear) film. The use of embedded electronics in a lens assembly introduces a potential requirement for communication with the electronics, for a method of powering and/or re-energizing the electronics including power control or power management circuitry, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years.

Vision correction, and potentially vision enhancement, is typically achieved in spectacle lenses, contact lenses, intraocular lenses (IOL's) and other ophthalmic devices through static optics. For example, spectacle lenses or contact lenses to treat myopia (nearsightedness) comprise lenses with spherical power to correct focus onto the retina caused by defects in the cornea and/or lens. Bifocal corrective lenses may contain an inset lens of a different power than the main lens. More advanced designs use gradient, zone, or other schemes to vary corrective power over the lens. However, because these lenses are optically static, they do not match the human eye's natural response which is a variable-focus action accomplished by varying the optical power of the eye's crystalline lens. In presbyopic individuals, the eye's natural ability to accommodate with different focal lengths is greatly reduced leading to a loss of function and annoyance. Recent advancements in the field have included spectacle lenses and even IOL's with some dynamic accommodation, for example, electronic spectacle lenses or IOL's connected to the eye's zonules to achieve a limited amount of optical power change. These existing systems are limited by only covering a small range of add power, perhaps only +1 diopter, requiring spectacle lenses to be worn, requiring surgery to implant an IOL, and other drawbacks.

There are several types of electronically variable lens technologies, including liquid crystal, electro-active polymer, electro-mechanical, variable fluid, and liquid meniscus lenses. Such electronically variable lenses require an actuator, and an electronic device to alter the focal length of the lens. For example, in a liquid meniscus or electro-active polymer lens, an applied voltage and/or current from an actuator modulates physical parameters of the lens to vary the focal length. Both variable lenses and their actuators, also known as lens drivers, are commercially available for various applications such as smartphone cameras and industrial applications. Suitable lenses and actuators do not exist for ophthalmic devices such as contact lenses and IOL's.

Electrical or powered lenses typically require higher voltage than what is immediately available from a battery. For example, a powered lens may require sixty (60) volts to reach the maximum change of focal length but typical batteries output less than four (4) volts. Typical lens drivers include a voltage multiplier circuit to achieve high output voltage from a low-voltage source, many designs of which are known in the art. A voltage multiplier is essentially a voltage and current conversion device, similar in principal to that of an electric transformer with mismatched primary-to-secondary ratios. Whereas a transformer operates on alternating current, a voltage multiplier operates from a direct current (DC) source such as a battery. A voltage multiplier may comprise a charge pump, a circuit type widely known in the electronics art.

Lens drivers which are presently available have many disadvantages which make them unsuitable for use in ophthalmic devices such as contact lenses and IOL's. Current consumption of typical lens drivers is on the order of approximately one (1) to more than one hundred (100) milliamps. While this is acceptable current consumption for a robotic manufacturing system with access to main line power or even a camera or smartphone with a relatively large battery, it is far too much current for a power source in an ophthalmic device. Such power sources, implemented as batteries, energy harvesters, and/or capacitors, are typically limited to current of perhaps thirty (30) microamps or less. Both the active current consumption, the current drawn by the lens driver when activating the powered lens, and the standby current consumption, the current drawn when the lens driver is not driving the powered lens, are critical parameters for an ophthalmic device.

Typical electronically variable lenses and their lens drivers are designed for applications and not optimized for ophthalmic device usage. For example, some lenses are continuously variable over a range of focal lengths from millimeters to infinity, some thirty (30) or more diopters. Commercial lenses and drivers must change focal length very quickly, perhaps within less than one hundred (100) milliseconds. Ophthalmic lenses may only need to change focus in one (1) or two (2) seconds, the time typically required for the natural eye to change focal distance, as is known in the art. With liquid meniscus lenses, even with the lens voltage charged in 100 milliseconds, the lens itself would take 1 to 2 seconds to change focus; however, with liquid crystal optics, a lens activation of 100 milliseconds is achievable and the optics will respond more quickly. Typical lens and driver systems intended for commercial and manufacturing applications must last for many years in operation and undergo wide changes in focal length many times per day. In contrast, some ophthalmic devices such as contact lenses may be disposable and only used for eighteen (18) hours.

Typical lens drivers are implemented with discrete electronics or integrated circuits (IC's). Even when implemented as IC's, lens drivers may require external components such as capacitors, and the physical die size of the lens driver may be two (2) square millimeters or more at a thickness of hundreds of microns and thus still a challenge.

Electrically variable lenses are typically activated with a voltage of ten (10) to sixty (60) volts. Thus, lens drivers for these devices must output a high voltage sufficient to activate the powered lens. Lens drivers may be programmable to change the output voltage thereby modulating the optical power of the powered lens.

Due to requirements for speed, reliability, and precise modulation of optical power over a large range of focal distances, typical lens drivers for liquid meniscus lenses utilize an alternating current (AC) driver. Such an AC driver rapidly switches the bias applied to the lens between positive and negative, perhaps at a one kilohertz (1 kHz) rate. Other types of optics may require lower frequencies, for example, 25 to 50 Hz. This drive method provides benefits for existing commercial applications, but also greatly increases current consumption from the alternative direct current (DC) drive method. The liquid meniscus lens may be modeled as a capacitor, and as such the energy required to charge the capacitor is $\frac{1}{2} \times C \times V^2$ where C is the lens capacitance and V is the applied voltage. Liquid lens capacitance is approximately two hundred picofarads (200 pF). It is apparent that a large amount of power is provided and consumed by a typical high-voltage lens driver since the lens capacitance must be charged at a fast rate.

Accordingly, there exists a need for a lens driver for a powered ophthalmic lens that is optimized for low cost, long-term reliable service, safety, size, and speed while providing the requisite power to drive a variable-focus optic.

SUMMARY OF THE INVENTION

The lens driver, including the high-voltage H-bridge control circuit for powering a variable-focus optic electronic ophthalmic lens, of the present invention overcomes the disadvantages associated with the prior art as briefly set forth above.

In accordance with one aspect, the present invention is directed to an ophthalmic apparatus. The ophthalmic apparatus comprising an ophthalmic lens for use in at least one of in or on the eye; an optic element incorporated into the ophthalmic lens, the optic element configured for at least one of vision correction and vision enhancement and having one or more of electronically controlled focal length, electronically controlled light transmission, and electronically controlled polarization; and an electronic system incorporated into the ophthalmic lens, the electronic system including: a power source; an H-bridge circuit configured to control a voltage supplied to the optic element, to reverse the polarity of a voltage supplied to the optic element and to short the optic element, the H-bridge circuit including first and second lower switches implemented as N-channel MOSFET transistors, and first and second upper P-channel MOSFET switches; an H-bridge control circuit used to control the first and second upper P-channel MOSFET switches using level shifter cells and configured to be a high-impedance circuit thereby preventing a loading of the power source, the level shifter cells comprising buffers, a capacitor coupling circuit, and a charge pump cell, wherein the capacitors level shift between a low voltage and a high voltage and transfer the charge to the charge pump cell, the charge pump cell provides an activation voltage for the first and second upper P-channel MOSFET switches, and an active turn-off circuit comprising control switches designed to deactivate the first and second upper P-channel MOSFET switches as necessary by activating an additional level shifter circuit to activate the control switches, and a cross-coupled switch circuit between the outputs of the two level shifter cells thereby ensuring only one of the first and second upper P-channel MOSFET switches is on at a time; and a system controller configured to provide control and timing signals for the electronic system, wherein the power source provides a voltage to sources of the first and second upper P-channel MOSFET transistor and to the H-Bridge control circuit.

In accordance with another aspect, the present invention is directed to an ophthalmic apparatus. The ophthalmic apparatus comprising an ophthalmic lens for use in at least one of in or on the eye; an optic element incorporated into the ophthalmic lens, the optic element configured for at least one of vision correction and vision enhancement and having one or more of electronically controlled focal length, electronically controlled light transmission, and electronically controlled polarization; and an electronic system incorporated into the ophthalmic lens, the electronic system including: a power source; an H-bridge circuit configured to control a voltage supplied to the optic element, to reverse the polarity of a voltage supplied to the optic element and to short the optic element, the H-bridge circuit including first and second lower switches implemented as N-channel MOSFET transistors, and first and second upper P-channel MOSFET switches; an H-bridge control circuit used to control the first and second upper P-channel MOSFET switches using level shifter cells and configured to be a high-impedance circuit thereby preventing a loading of the power source, the level shifter cells comprising buffers, a capacitor coupling circuit, and a charge pump cell, wherein the capacitors level shift between a low voltage and a high voltage and transfer the charge to the charge pump cell, the charge pump cell provides an activation voltage for the first and second upper P-channel MOSFET switches, and an active turn-off circuit comprising control switches designed to deactivate the first and second upper P-channel MOSFET switches as necessary by activating a cross-coupled switch circuit between the outputs of the two level shifter cells thereby ensuring only one of the first and second upper P-channel MOSFET switches is on at a time; and a system controller configured to provide control and timing signals for the electronic system, wherein the power source provides a voltage to gates of the first and second upper P-channel MOSFET transistor and the to the H-Bridge control circuit.

In accordance with yet another aspect, the present invention is directed to an ophthalmic apparatus. The ophthalmic apparatus comprising an ophthalmic lens for use in at least one of in or on the eye; an optic element incorporated into the ophthalmic lens, the optic element configured for at least one of vision correction and vision enhancement and having one or more of electronically controlled focal length, electronically controlled light transmission, and electronically controlled polarization; and an electronic system incorporated into the ophthalmic lens, the electronic system including: a power source; a switching circuit configured to control a voltage supplied to the optic element and to short the optic element, the switching circuit including a lower switch implemented as an N-channel MOSFET transistor and an upper P-channel MOSFET switch; a switching control circuit used to control the upper P-channel MOSFET switch using a level shifter cell and configured to be a high-impedance circuit thereby preventing a loading of the power source, the level shifter cell comprising a buffer, a capacitor coupling circuit, and a charge pump cell, wherein the capacitor level shifts between a low voltage and a high voltage and transfer the charge to the charge pump cell, the charge pump cell provides an activation voltage for the upper P-channel MOSFET switch, and an active turn-off circuit comprising a control switch designed to deactivate the upper P-channel MOSFET switch as necessary by activating an additional level shifter circuit to activate the control switch; and a system controller configured to provide control and timing signals for the electronic system, wherein the power source provides a voltage to sources of the upper P-channel MOSFET transistor and to the H-Bridge control circuit.

In accordance with still yet another aspect, the present invention is directed to an electronic system. The electronic system comprising a power source; an H-bridge circuit configured to control a voltage supplied to the optic element, to reverse the polarity of a voltage supplied to the optic element and to short the optic element, the H-bridge circuit including first and second lower switches implemented as N-channel MOSFET transistors, and first and second upper P-channel MOSFET switches; an H-bridge control circuit used to control the first and second upper P-channel MOSFET switches using level shifter cells and configured to be a high impedance circuit thereby preventing a loading of the power source, the level shifter cells comprising buffers, a capacitor coupling circuit, and a charge pump cell, wherein the capacitors level shift between a low voltage and a high voltage and transfer the charge to the charge pump cell, the charge pump cell provides an activation voltage for the first and second upper P-channel MOSFET switches, and an active turn-off circuit comprising control switches designed to deactivate the first and second upper P-channel MOSFET switches as necessary by activating an additional level shifter circuit to activate the control switches, and a cross-coupled switch circuit between the outputs of the two level shifter cells thereby ensuring only one of the first and second upper P-channel MOSFET switches is on at a time; and a system controller configured to provide control and timing signals for the electronic system, wherein the power source provides a voltage to sources of the first and second upper P-channel MOSFET transistor and the to the H-Bridge control circuit.

The present invention relates to a powered contact lens comprising an electronic system which performs any number of functions, including actuating a variable-focus optic. The electronic system includes one or more batteries or other power sources, power management circuitry, one or more sensors, clock generation circuitry, control circuitry implementing suitable control algorithms, and lens driver circuitry.

The lens actuator or lens driver circuitry generates the appropriate bias to actuate a variable-focus optic. It is activated by the system controller, control system, or control circuitry, receives current from the power management circuitry, and receives a clock signal from the clock generation circuitry. The lens actuator or lens driver circuitry comprises one or more power sources, one or more bias generators and one or more switching circuits. The lens driver circuitry converts battery-level voltage to a bias appropriate to actuate the variable-focus lens. It also includes circuitry to switch bias to the variable-focus lens, for example, ground, high voltage, polarity reversal, and floating.

In one exemplary embodiment, the variable-focus optic is an electro wetting device which requires a high voltage to change focus. The lens driver for such a variable-focus optic converts the battery-level voltage to a high-voltage bias, for example, a 25 V output from a 2 V input. In another exemplary embodiment, the variable-focus optic is an electro-mechanical or electro-fluid device. The lens driver for such a variable-focus optic may be substantially different from that required for an electro wetting device, for example, requiring a specific driving waveform and feedback of the lens or optic state. However, the function in the ophthalmic device is the same; namely, electronically controlling the focal length of a variable-focus optic of a lens. In yet another exemplary embodiment, the variable-focus optic may comprise a liquid crystal device requiring a current-mode bias. The current invention is not utilizing this current mode-bias, but it is possible and may have certain uses and benefits.

The lens driver circuitry of the present invention offers safe, low cost, long term, reliable power in a package sized for utilization on or in an ophthalmic device, such as a contact lens, without significant impact on comfort or wearability.

To reduce current consumption, several techniques in accordance with the present invention are used which are applicable to a lens driver for an ophthalmic device. Current is reduced by carefully matching the requirements of the lens driver to the variable-focus optic of the powered lens, with the variable-focus optic of the powered lens requirements matched to those of an ophthalmic device. For example, to avoid switching losses for a liquid meniscus lens, a DC drive is used instead of an AC drive. This is possible because, in some exemplary embodiments, continuously variable focus is not needed or is substantially different than the requirements for existing lens drivers. Add power may be simply plano (0 add power) and +3 optical power. Further, the design of a specific liquid meniscus lens for an ophthalmic device reduces or eliminates the need for polarity toggling. In some exemplary embodiments, the lens driver's output is unregulated and not part of a control loop. While tight regulation of the lens driver output may be required for applications covering a wide range of focal lengths, tight regulation is not necessarily required for all ophthalmic applications. The design of the lens may allow a wide range of driver voltages to accomplish the desired change in focal length. As would be appreciated by one skilled in the art, removal of the feedback system greatly simplifies the lens driver with corresponding improvements in die size and current consumption.

Current consumption is further reduced by carefully designing the lens driver for the ophthalmic application. Active current is reduced to approximately three (3) microamperes. Standby and storage current is reduced to nanoamperes or picoamperes. This accomplished through techniques which are known in the art as well as innovative new techniques as described in greater detail herein.

Designing the lens driver together with the lens for an ophthalmic application permits additional improvements in the lens driver. The activation voltage of the variable-focus optic of the powered lens may be reduced, with a corresponding reduction in the output voltage requirements of the lens driver, and the lens driver's current and size. The capacitance and resistance of the variable-focus optic of the powered lens may be optimized, thereby requiring less current from the lens driver. Again, this reduces the lens driver's size and current consumption.

Size and packaging are of critical importance to the suitability of a lens driver for an ophthalmic application. As such, the integration, layout, and interconnects are designed particularly for use in ophthalmic applications. All components of the lens driver are integrated onto one silicon integrated circuit or IC, eliminating the need for external components such as discrete surface-mount capacitors. It is important to note however, that external components may be required. Die size is reduced through various techniques. Interconnects are added in wafer post-processing and designed specifically for an ophthalmic application. Die are thinned, perhaps to thirty (30) to one hundred (100) microns.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
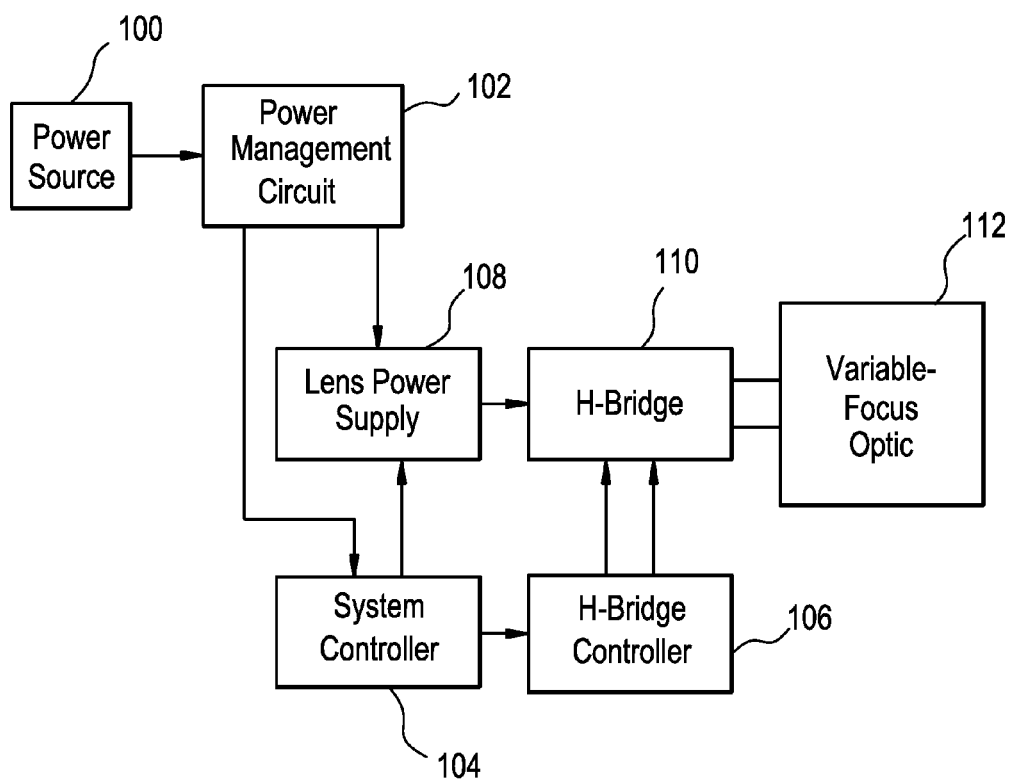
FIG. 1 is a block diagram representation of an exemplary variable-focus lens system in accordance with the present invention.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light emitting diodes, and miniature antennas may be integrated into contact lenses via custom built optoelectronic components to not only correct vision, but to enhance vision as well as provide additional functionality as is explained herein. Electronic and/or powered contract lenses may be designed to provide enhanced vision via zoom-in and zoom-out capabilities or just simply modifying the refractive capabilities of the lenses. Electronic and/or powered contact lenses may be designed to enhance color and resolution, to display textural information, to translate speech into captions in real time, to offer visual cues from a navigation system, to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium and potassium levels as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The present invention is directed to a powered ophthalmic lens or powered contact lens comprising an electronic system, which actuates a variable-focus lens or any other device or devices configured to implement any number of numerous functions that may be performed. The electronic system includes one or more batteries or other power sources, power management circuitry, one or more sensors, clock generation circuitry, control circuitry implementing suitable control algorithms, and lens driver circuitry. The complexity of these components may vary depending on the required or desired functionality of the lens.

The lens driver circuitry generates the appropriate bias to actuate a variable-focus lens. It is activated by the system controller or control circuitry, receives current from the power management circuitry, and receives a clock signal from the clock generation circuitry. The lens driver circuitry comprises one or more power sources, one or more bias generators and one or more switching circuits. The lens driver circuitry converts battery-level voltage to a bias appropriate to actuate the variable-focus lens. It also includes circuitry to switch bias to the lens, for example, ground, high voltage, polarity reversal, and floating.

As set forth above, the present invention relates to an ophthalmic device such as a contact lens comprising a number of components, with the lens driver being one of these components. The proper combination of devices could yield potentially unlimited functionality; however, there are a number of difficulties associated with the incorporation of extra components on a piece of optical-grade polymer that makes up the contact lens. In general, it is difficult to manufacture such components directly on the lens for a number of reasons, as well as mounting and interconnecting planar devices on a non-planar surface. It is also difficult to manufacture to scale and form. The components to be placed on or in the lens need to be miniaturized and integrated onto just 1.5 square centimeters of a transparent polymer, or more particularly, seventeen (17) square millimeters, while protecting the components from the liquid environment on the eye. It may also be difficult to make a contact lens comfortable for the wearer with the added thickness of additional components.

In addition to the size requirements set forth herein, electronic devices incorporated into a contact lens have to be robust and safe for use in an essentially aqueous environment. Tears have a pH of about 7.4 and are about 98.2 percent water and 1.8 percent solids, including electrolytes such as sodium, potassium, calcium, magnesium, and chlorides. This is a somewhat harsh environment in which to introduce electronics. Also, contact lenses are generally designed to be worn for at least four hours and preferably longer than eight hours. Electronic components require energy. This energy may be supplied from any number of sources, including built-in batteries. Since batteries and other potential energy sources have limited potential at these sizes, all electronic components, including the lens driver, are preferably designed to consume as little power as possible so that the contact lenses may be worn for a given period of time even after sitting idle for a given period of time (shelf life). Finally, all components in an electronic contact lens have to be biocompatible and safe. Accordingly, all electronics incorporated into the contact lens have to meet all of the above design parameters; namely, size, survivability in an aqueous solution, power consumption and safety. The lens driver of the present invention meets all of these requirements.

It is important to note that there are many alternate exemplary embodiments of variable-focus optics. For example, the variable-focus optic may be implemented utilizing liquid crystal technology, electro-active polymer technology, variable fluid technology and liquid meniscus technology. In the following detailed description, the variable-focus optic comprises a liquid meniscus lens. As set forth above, alternative embodiments for the variable-focus optic may be utilized, including a liquid crystal optic; however, what is important is that the circuitry described with respect to the present invention; namely, the H-bridge and H-bridge controller may be utilized with any of these variable-focus optics. The term "liquid meniscus" and "electro-wetting" as set forth herein, are utilized interchangeably in this specification. In order to better understand the description of exemplary embodiments of the present invention, a general overview of a liquid meniscus lens is given. A typical liquid lens comprises a cell that includes two immiscible liquids. One liquid is insulating and non-polar while the second liquid is typically a conducting water solution, such as a saline solution. Both liquids are transparent with different indexes of refraction. Preferably, both liquids have the same density such that gravity has minimal impact on lens operation. The insulating liquid is configured in the shape of a drop and placed in contact with a thin insulating window which is hydrophobic so that the insulating liquid will sit upon it. The conducting liquid is also placed in contact with the insulating window and the insulating liquid. A transparent electrode is positioned on the external side of this window. The application of a voltage between the electrode and the conducting liquid favors the wettability of the surface of this same liquid thereby deforming the interface and changing the shape of the insulating liquid drop, thereby changing the focal length of the lens. This is a high level description and not intended to be construed as the specific optic element of the present invention.

In one exemplary embodiment, the variable-focus optic is an electro wetting device which requires a high voltage to change focus. High voltage may be required, for example, to deform the liquid meniscus system to the desired contact angle and refraction given the electro-wetting properties of the insulating and conductive liquids along with the properties of the insulating window. The lens driver for such a variable-focus optic converts the battery-level voltage to a high-voltage bias, for example, a 25 V output from a 2 V input. In another exemplary embodiment, the variable-focus optic is an electro-mechanical or electro-fluid device. The lens driver for such a variable-focus lens may be substantially different from that required for an electro-wetting device, for example, requiring a specific driving waveform and feedback of the lens state. However, the function in the ophthalmic device is the same; namely, electronically controlling the focal length of a lens. In yet another exemplary embodiment, the variable-focus lens may comprise a liquid crystal device requiring a current-mode bias.

An electro wetting lens possesses a certain amount of capacitance which arises from the physical construction of the lens. A conductive saline phase is connected to one electrical contact of the lens. A dielectric separates this conductive saline phase from an electrode which connects to the second electrical terminal of the lens. Thus, a capacitance arises between the two terminals due to the relative permittivity and thickness of the dielectric along with the area of the saline overlapping the electrode. In order to actuate the electro wetting lens, the capacitance must be charged until the terminal voltage exceeds the threshold of focal change activation. As such, the capacitance of the electro-wetting lens is of critical importance to the design of the lens driver. As is known to those skilled in the art, design parameters of a lens driver may be optimized to account for the lens load and expected performance requirements. For example, with a charge pump lens driver creating a high voltage to actuate an electro-wetting lens, an increase in one or more of clock frequency and capacitor size allows the charge pump to supply more current. Also as known in the art, an increase in current sourcing capability allows a capacitor to be charged faster. As such, the clock frequency and capacitor sizes of the lens driver may be optimized for electrical efficiency and actuation time for a variable-focus lens. Similar design connections exist for other electrically variable lenses and the corresponding lens drivers.

As stated above, it is important to note than any suitable variable optic may be utilized. In the examples above, a liquid meniscus optic is described; however, liquid crystal optics may be preferable. In addition to offering electronically controlled focal length, liquid crystal optics may also offer electronically controlled light transmission and polarization. In these cases, rather than modulating the refractive index of the liquid crystal or otherwise modulating the focal length of the optic, voltage applied to the liquid crystal lens modulates the light transmission percentage and/or state of polarization. The H-bridge control circuit of the present invention may be utilized with any number of optics and thus the description given below relates to the circuitry itself rather than the optics.

Referring now to FIG. 1, there is illustrated an exemplary embodiment of a variable-focus electronic ophthalmic lens system comprising a power source 100, a power management circuit 102, a system controller 104, an H-bridge-controller 106, a lens power supply 108, an H-bridge 110 and a variable-focus lens 112. The variable-focus lens 112 may be a liquid lens that changes focal properties, e.g. focal length, in response to an activation voltage applied across two electrical terminals of the lens. As set forth above, any suitable technology may be utilized. The two terminals may correspond to a front-side and a back-side terminal of the optic 112. The activation voltage may be significantly higher than voltages available from the power source, for example, twenty-five (25) volts for full lens activation and a battery providing only two (2) volts. The power source 100 may be a battery, a capacitor or similar device providing stored charge at a usable working voltage. In some exemplary embodiments, the power source 100 may be an inductive power coupling to an external power supply. The power management circuit 102 may comprise one or more voltage regulators, voltage or current references, and switches to selectively enable power supplied to other components in the electronic lens system. The system controller 104 comprises a digital control system implemented as either a microcontroller running software, or in digital logic, such as a state machine, and may further comprise an oscillator for generating a periodic timing signal for the control system. The system controller 104 provides control signals to the lens power supply 108 and to the H-bridge controller 106 based on an internal algorithm or under external control by a user (interface not shown). The lens power supply 108 receives current at a low working voltage from the power source 100 and generates a high output voltage at or above the activation voltage of the variable-focus lens 112, i.e. sufficient to change the state of the variable-focus lens 112. The lens power supply 108 may further comprise an oscillator or receive a clock signal from the system controller 104. In the present exemplary embodiment, the lens power supply 108 output is coupled to the variable-focus lens 112 through the H-bridge switch circuit 110, a circuit type widely known in the art. The H-bridge 110 comprises switches between the lens power supply 108 output and each of the variable-focus lens 112 terminals and between each of the variable-focus lens 112 terminals and an electrical ground of the system. The state of the H-bridge 110 is determined by one or more of the system controller 104 control signals applied to the H-bridge controller 106. The H-bridge controller 106 acts to interface the H-bridge 110 to the system controller 104. Generally, an H-bridge controller 106 will level-shift the control signals from a low-voltage digital controller, for example system controller 104, which runs at a typical voltage of 1.8 volts, to the high-voltage H-bridge 110. The H-bridge controller 106 may also include timing and delay circuitry, circuitry to manage outputs to the H-bridge 110 with fewer inputs from the system controller 104, and circuitry to prevent problematic states in the H-bridge 110 such as shoot-through, a short-circuit condition known in the relevant art. The H-bridge 110 may be configured into one or more states such as with the lens terminals open, shorted to ground, or powered with one terminal coupled to the lens power supply 108 output and the other to ground, or powered in the opposite polarity. The H-bridge 110 provides a convenient method to energize the variable-focus lens 112 for actuation, discharge the variable-focus lens 112 to return it to a base power, and toggle the polarity of bias provided to the variable-focus lens 112. Grounding both terminals of the variable-focus optic allows charge in the lens 112 to be quickly removed, thereby allowing the variable-focus lens 112 to quickly change to the non-energized focus state instead of suffering a long delay as charge slowly dissipates through a high-isolation system. The system controller 104 may periodically reverse the polarity of the H-bridge 110 output to optimize the performance of the variable-focus lens 112, for example, to avoid excessive charge trapping that may occur when powered in one state for too long. It is important to note that the functional blocks are shown and described for illustrative purposes only, and that functional blocks may be added, removed or substituted while still relying on the basic principles of a lens driver designed and configured specifically for use in an electronic or powered ophthalmic device as described herein.

Figure 2:
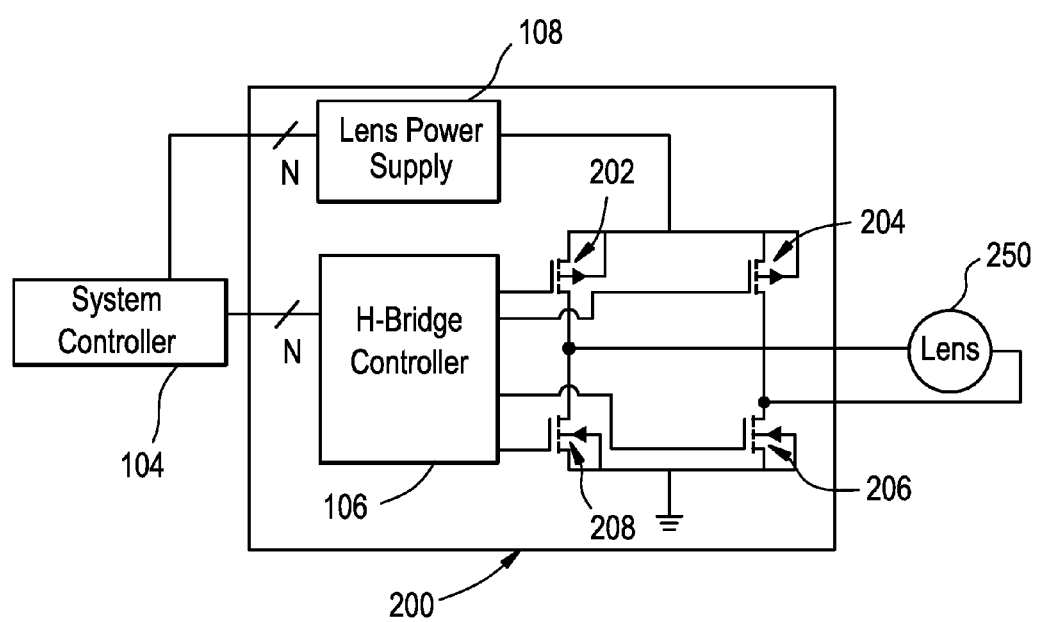
FIG. 2 is a diagrammatic representation of an exemplary H-bridge circuit coupled to a powered contact lens having a variable-focus optic in accordance with the present invention.

FIG. 2 illustrates an exemplary H-bridge circuit 200 coupled to a powered ophthalmic device having a variable-focus lens 250. The H-bridge circuit 200 is particularly useful for controlling the voltage potential applied to the variable-focus lens 250 and may be used to switch voltage to the variable-focus lens 250, reverse polarity across the variable-focus lens 250, and ground the variable-focus lens 250. The exemplary H-bridge 200 comprises metal-oxide-semiconductor field-effect transistor (MOSFET) switches 202, 204, 206 and 208 which are controlled by an H-bridge controller 106 and a system controller 104. The system controller 104 could be replaced by a state machine or other device capable of controlling the lens driver circuitry. The H bridge controller 106 is the interface between the system controller 104 and the H-bridge, for example, shifting voltage from a 1.8 V logic level to the gate drive needed for a 25 V output. It is important to note that the low-voltage logic level may be as low as about 0.9 volts and the high-level gate drive voltages may vary between 13 to 60 volts. It will be apparent to those skilled in the art that unique requirements exist for the voltages applied to the gates of the MOSFET switches 202, 204, 206 and 208 forming the H-bridge. Put another way, the low-level output voltages from a typical system controller are insufficient to turn off the high-side switches 202 and 204. The H-bridge controller 106 provides the necessary level and control translation to operate these high-side switches. It is also necessary to optimize current consumption by ensuring no two switches on the same leg (202 and 208, or 204 and 206) are closed at the same time. The variable-focus lens 250 connects to the outputs of the H-bridge. The H-bridge inputs connect to the lens power supply 108 and to ground. The lens power supply 106 may be a voltage multiplier, charge pump, or other circuit. Additional circuitry (not illustrated) may be required for implementation and control of the H-bridge 110 depending on the requirements thereof and the technology utilized for implementation thereof. For example, additional switches may be required depending on the lens power supply output level and the bias voltages available in the system.

In typical operation, one side of the variable-focus lens 250 will be connected to ground while the other side is connected to the lens power supply 108. To accomplish this, the switches 202, 204, 206 and 208 forming the H-bridge are activated in the correct on/off combination. For example, if switches 202 and 206 are closed while switches 204 and 208 are open, the left side of the variable-focus lens 250 will connect to the lens power supply 108 and the right side of the variable-focus lens 250 will connect to ground. This represents one case where the variable-focus lens 250 may be charged and thus activated. An alternate case is one in which the variable-focus lens is charged in the opposite polarity, closing switches 204 and 208 while setting switches 202 and 206 to open. To deactivate the variable-focus lens 250, switches 202 and 204 are set open while switches 208 and 206 are closed. This eliminates any voltage potential across the variable-focus lens 250, which causes it to deactivate. Another potentially useful state is to apply a potential across the variable-focus lens 250, allow the variable-focus lens 250 to accumulate charge, then disconnect the variable-focus lens 250 and allow it to remain activated on stored charge only. This may be implemented by opening all switches 202, 204, 206 and 208 forming the H-bridge. Such a state may allow a further reduction in current consumption if the lens power supply 108 is disabled while the variable-focus lens 250 is floating. Careful design of the variable-focus lens 250 capacitance and resistance, and leakage in the electronic system may allow the variable-focus lens 250 to store charge for many seconds, thereby greatly reducing the duty cycle of the lens power supply 108 and hence the average current consumption.

Figure 3:
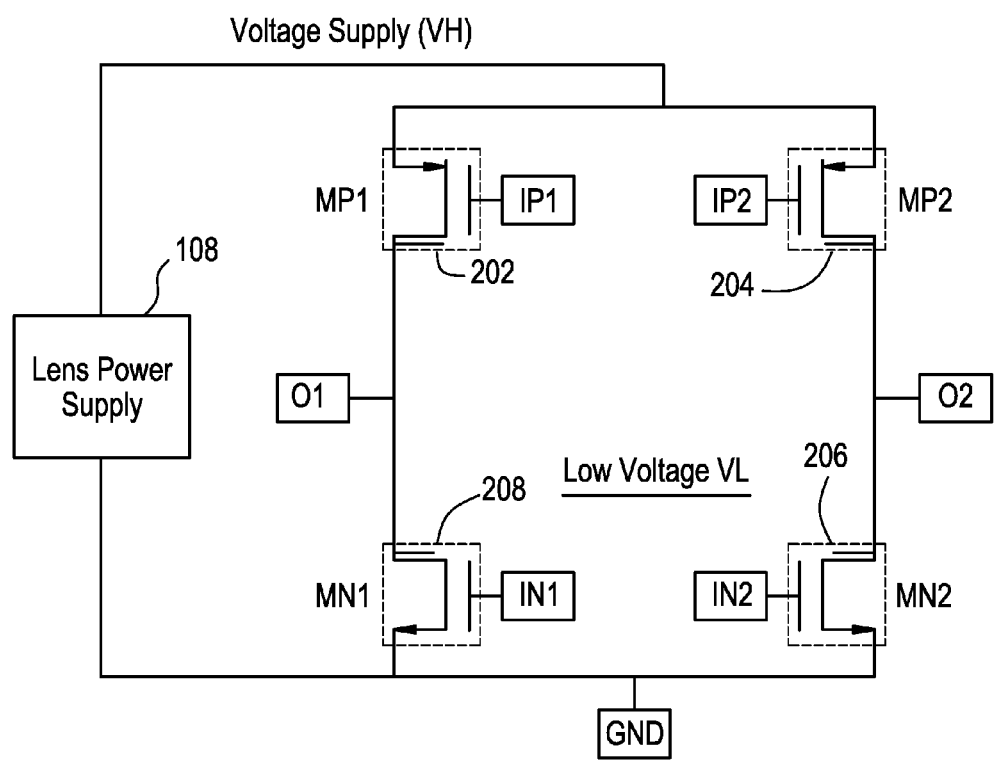
FIG. 3 is a diagrammatic representation of the exemplary H-bridge circuit of FIG. 2.

In order to better illustrate the present invention, a simplified diagrammatic representation of the H-bridge circuit 200 of FIG. 2 is illustrated in FIG. 3. A lens power supply 108 is required to activate the variable-focus lens (not shown). The lens power supply 108 may be implemented in any number of ways, for example, via a charge pump as set forth above. The variable-focus lens also requires a set of switches, the H-bridge circuit, to apply a VH voltage from the lens power supply 108 in a forward or positive polarity and a reverse or negative polarity to the lens, as well as the ability to short the variable-focus lens terminals. The forward and reverse polarity switching is accomplished using a standard H-bridge circuit comprising four switches implemented as MOSFETs, two of the switches being NMOS (N-channel) switches 208 and 206 referenced to the lowest potential (GND) and two PMOS (P-channel) switches 202 and 204 referenced to the highest potential, VH, from the lens power supply 108. The load, for example, the variable-focus lens is connected at the O1 and O2 terminals. Both sets of switches require a control voltage, VC, to be applied to open or close a particular switch and to have it set as opened or closed, i.e. VC equal to 0 to open a particular switch. The control circuit voltage, VC, is derived from the logic power supply voltage, VL, not shown. The NMOS switches 208 and 206 require IN1 or IN2 to be VC above the reference GND to be closed and the PMOS switches 202 and 204 require IP1 or IP2 to be VC below the reference VH to be closed.

To achieve a forward polarity on the variable-focus lens where O1 is at the VH potential and O2 is at the GND potential, IP1 is set to the potential VH minus VC. This closes PMOS switch 202 and connects O1 to VH. IN2 is set to the VC plus GND potential which activates NMOS switch 206 and connects O2 to GND, IP2 is set to the potential VH which opens PMOS switch 204, and IN1 is set to GND potential which opens NMOS switch 208. To achieve a reverse polarity on the variable-focus lens where O1 is at GND potential and O2 is at the VH potential, IP1 is set to the VH potential which opens PMOS switch 202, IN2 is set to GND potential which open NMOS switch 206. IP2 is set to the potential VH minus VC which closes PMOS switch 204 and connects O2 to VH, and IN1 is set to VC plus GND potential which closes NMOS switch 208 and connects O1 to GND.

In general with this type of H-bridge circuit, there is no problem with applying the VC voltage to the NMOS switches 208 and 206 since VC is slightly above ground and within the voltage range of typical digital control signals. However, applying the VC voltage to the PMOS switches 202 and 204 is more complicated, since it is a high voltage beyond that of typical digital control signals, and requires a novel approach while also conforming to the additional requirements of an ophthalmic application as described herein. One solution would be to utilize level shifters implemented as resistor dividers and/or capacitor dividers. Another solution would be to utilize cross-coupled level shifters. However, because an ophthalmic application such as that described herein is sensitive to supply current and die area, the requirements for a suitable level shifter include no or low steady-state current loading on the VH in either the high or low state, low to no latch-up or unknown state issues, no additional voltage rails or levels, safe operating conditions for all components, low complexity, and sufficient switching times which is important, but not critical. Currently utilized implementations provide the function of a level shifter, but no currently known design satisfies all of the requirements described herein.

The exemplary H-bridge circuit of the present invention satisfies all of the above-described requirements; namely, a circuit that can develop the appropriate VC voltage to drive the PMOS switches, and circuitry that can turn off either or both of the PMOS switches while providing a no steady-state current drain, a low chance of an unknown state and low complexity. The exemplary circuitry to control the PMOS switches is a level shifter cell that creates approximately a VL or logic supply voltage across it as the VC voltage, and when referenced to the VH, it creates a VH minus VC as the gate to source voltages, vgs_MP1 and vgs_MP2, to close the PMOS switches. In addition, complete shut-off of the switches is imperative, thus an additional circuit is used to force both vgs_MP1 and vgs_MP2 voltages to zero (shorting), and just force the opposite switch off by forcing the gate to source voltage for that switch to zero volts. The exemplary H-bridge circuit further comprises an additional level shifter cell to force both switches off. A complete and detailed description is given below.

Figure 4:
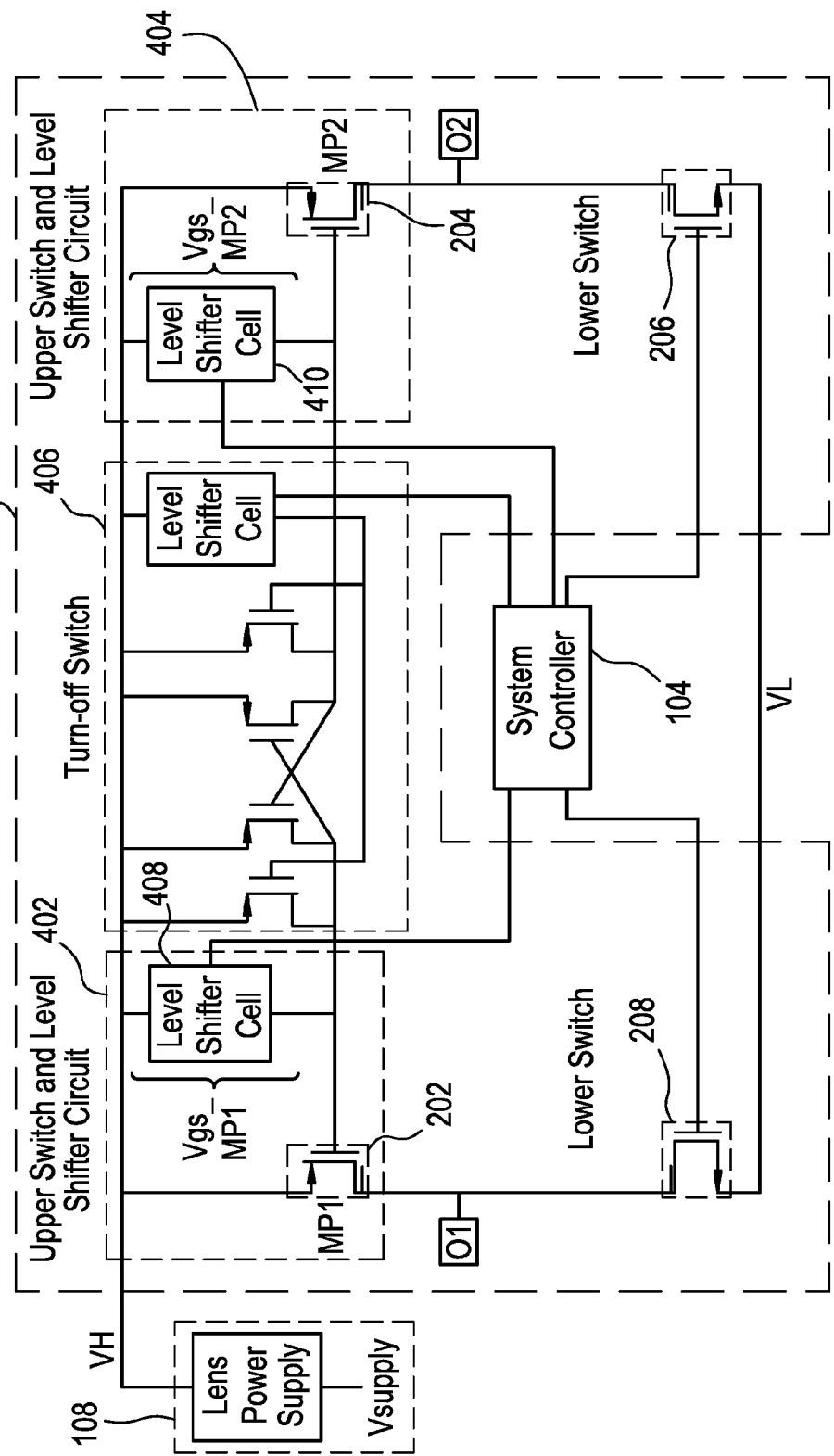
FIG. 4 is a diagrammatic representation of a first exemplary H-bridge/H-bridge controller circuit in accordance with the present invention.

Referring to FIG. 4, there is illustrated a diagrammatic representation of a first exemplary embodiment of an H-bridge/H-bridge controller circuit 400 in accordance with the present invention. Also illustrated in FIG. 4 are the system controller 104 and the lens power supply 108. The H-bridge/H-bridge controller circuit 400 comprises two upper switch and level shifter circuits 402 and 404, lower NMOS switches 206 and 208, and turn-off switch circuit 406. Each upper switch and level shifter circuits 402 and 404 comprises a PMOS switch 202 and 204 and level shifter cells 408 and 410 respectively. A detailed description of each of the components described herein is given below.

Figure 5:
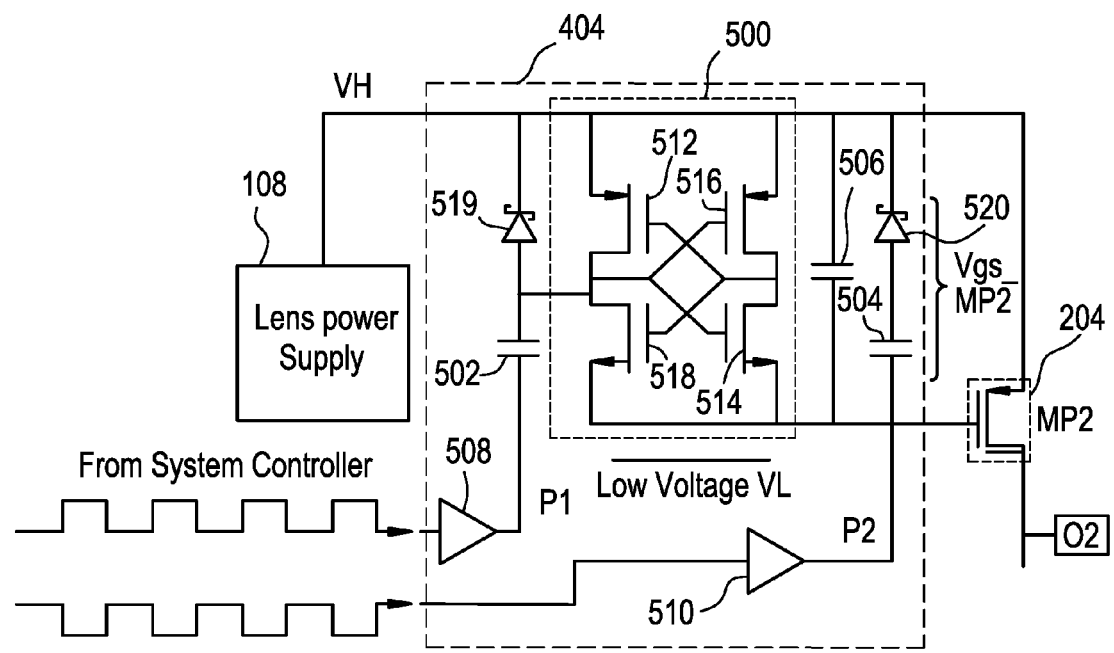
FIG. 5 is a diagrammatic representation of an upper switch and level shifter circuit of the first exemplary H-bridge/H-bridge controller circuit of FIG. 4.

FIG. 5 is a diagrammatic representation of upper switch and level shifter circuit 404, which is identical in construction and operation to upper switch and level shifter circuit 402. For ease of explanation, a description of only circuit 404 is given. The upper switch and level shifter circuit 404 comprises buffers, a capacitor coupling circuit and a charge pump cell 500 described in detail subsequently. The buffers 508 and 510 provide isolation from the system controller 104 and provide the proper drive necessary to the capacitors. The capacitors level-shift the signals between VL to VH and transfer charge to the charge pump cell. The only active current is through these capacitors, but since the charge pump is either adding charge or somewhat neutral, the loading caused by the level shifting is either acting as a source, as opposite of a load, or as a very high impedance load. This feature or functionality solves an important requirement for this upper switch and level shifter circuit 404; namely, it is high impedance and does not load the lens power supply 108. In addition, no other power supplies are required, the start-up does not suffer from latch up or ramping issues, and the overall design is fairly simple.

It is important to note that any number of charge pump cell circuits may be utilized in accordance with the present invention. In the exemplary embodiment illustrated in FIG. 5, the level shifter cell comprises a cross-coupled charge pump cell 500 in which there are two level-shift capacitors 502 and 504, driving the cell 500, one on each clock edge as detailed below. This cross-coupled charge pump cell is not unique in of itself, and other designs may be utilized. The result is a transfer of charge from the VL power supply to capacitor 506 thereby creating the VC voltage referenced to VH since one side of capacitor 506 is tied to VH. The VC voltage is now level shifted and the PMOS switch 204 may be operated efficiently and within the transistor specifications.

Driver buffer 508 receives an input from the system controller 104 and creates a square wave output at P1, switching between VL and GND in magnitude. Driver buffer 510 receives an input from the system controller 104 and creates a square wave output at P2 which is the same as P1 but 180 degrees out of phase with P1. When P1 is going from low to high, the charge from capacitor 502 is transferred to VH via active transistor 512, thus adding the charge to VH. Simultaneously, P2 is going from high to low causing capacitor 504 to pull current from capacitor 506 through the now active transistor 514, thus adding charge to and increasing the voltage across capacitor 506. During the opposite cycle, when P2 goes low to high, the charge from capacitor 504 is transferred to capacitor 506 via an active transistor 516, thereby adding charge to VH (keeping the circuit charge neutral). Simultaneously, P1 is going high to low causing capacitor 502 to pull the current from capacitor 506 through now active transistor 518, again adding charge to capacitor 506.

This process continually increases the voltage on capacitor 506, through several cycles, to the required VC or vgs_MP2 voltage. Because there is charge added to the VH node on one side and simultaneously the other side of the capacitor 506 is being charged by the negative going coupling capacitor, the net change in charge on VH is about zero, giving it a very low steady-state current, thereby the level shifter is looking like a very high impedance relative to the VH supply.

Schottky Diodes 519 and 520 are used to suppress the unwanted effects of the parasitic PNP device from between the drain (P), body (N), and substrate (P) in the PMOS devices 512 and 516. During the initial charging, the drain can be at higher potential than the body, thus activating this parasitic PNP which will significantly load the circuit with a shunt path back to ground (substrate). The diodes 519 and 520 act to shunt the drain to body junction of the parasitic PNP because the forward voltage is lower, thus preventing the parasitic PNP from activating.

Figure 6:
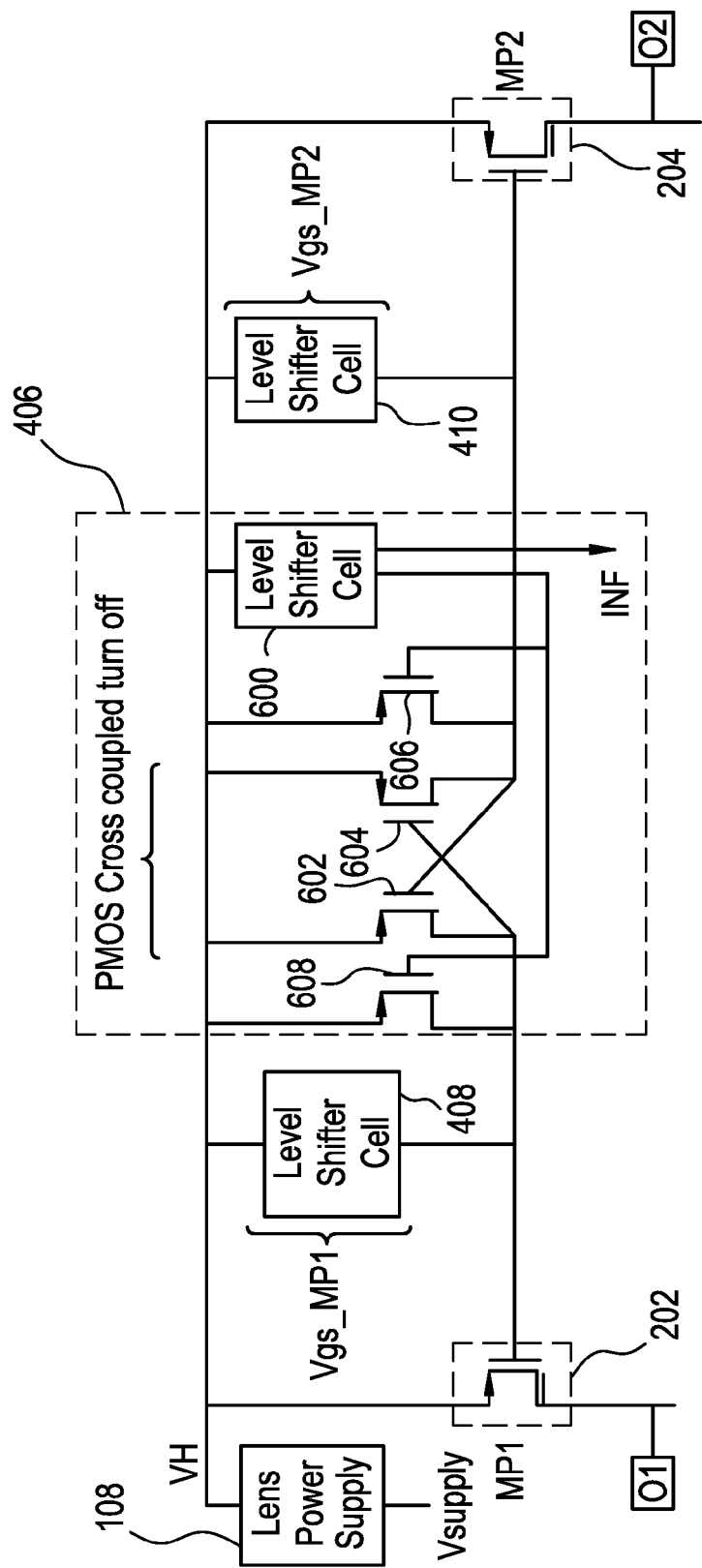
FIG. 6 is a diagrammatic representation of the turn-off switch circuit of the first exemplary H-bridge/H-bridge controller circuit of FIG. 4.

Referring now to FIG. 6, there is illustrated a diagrammatic representation of turn-off switch circuit 406. The turn-off switch circuit 406 comprises a level shifter cell 600 and a deactivation circuit. Activating the switch with the charge pump of the level shifter cell is straight forward; however, the charge pump does not shut off quickly after the activation signal is removed. Accordingly, another circuit, the deactivation circuit, is required to deactivate the PMOS portion of the H-bridge switch. Also illustrated in FIG. 6 are the lens power supply 108, the two PMOS switches 202 and 204 as well as level shifter cells 408 and 410.

There are two parts to the deactivation circuit as illustrated in FIG. 6. One deactivation circuit comprises transistors 602 and 604, wherein this circuit deactivates the side that is not activated, but cannot deactivate both at the same time. For example, if level shifter cell 408 is activated thereby activating PMOS switch 202, and level shifter cell 410 is deactivated, vgs_MP1 is sufficient to also activate transistor 604 and cause the vgs_MP2 to go to zero thereby deactivating PMOS switch 204 completely. Conversely, if level shifter cell 410 is activated thereby activating PMOS switch 204, and level shifter cell 408 is deactivated, vgs_MP2 is sufficient to also activate switch 602 and cause the vgs_MP1 voltage to go to zero thereby deactivating PMOS switch 202 completely.

Since this only works if one side is active, another circuit is required to turn off both sides at once. This circuit consists of PMOS transistors 606 and 608, and level shifter cell 600. Applying a differential pulse waveform to INF (in the same way that is used in FIG. 5 for the main switch activation, that is, two square waves that are 180 degrees out of phase) causes the level shifter cell 600 to create a voltage across the circuit thereby activating both transistors 606 and 608, which in turn, deactivates both PMOS switches 202 and 204 by shorting the vgs_MP1 and vgs_MP2 signals.

Figure 7:
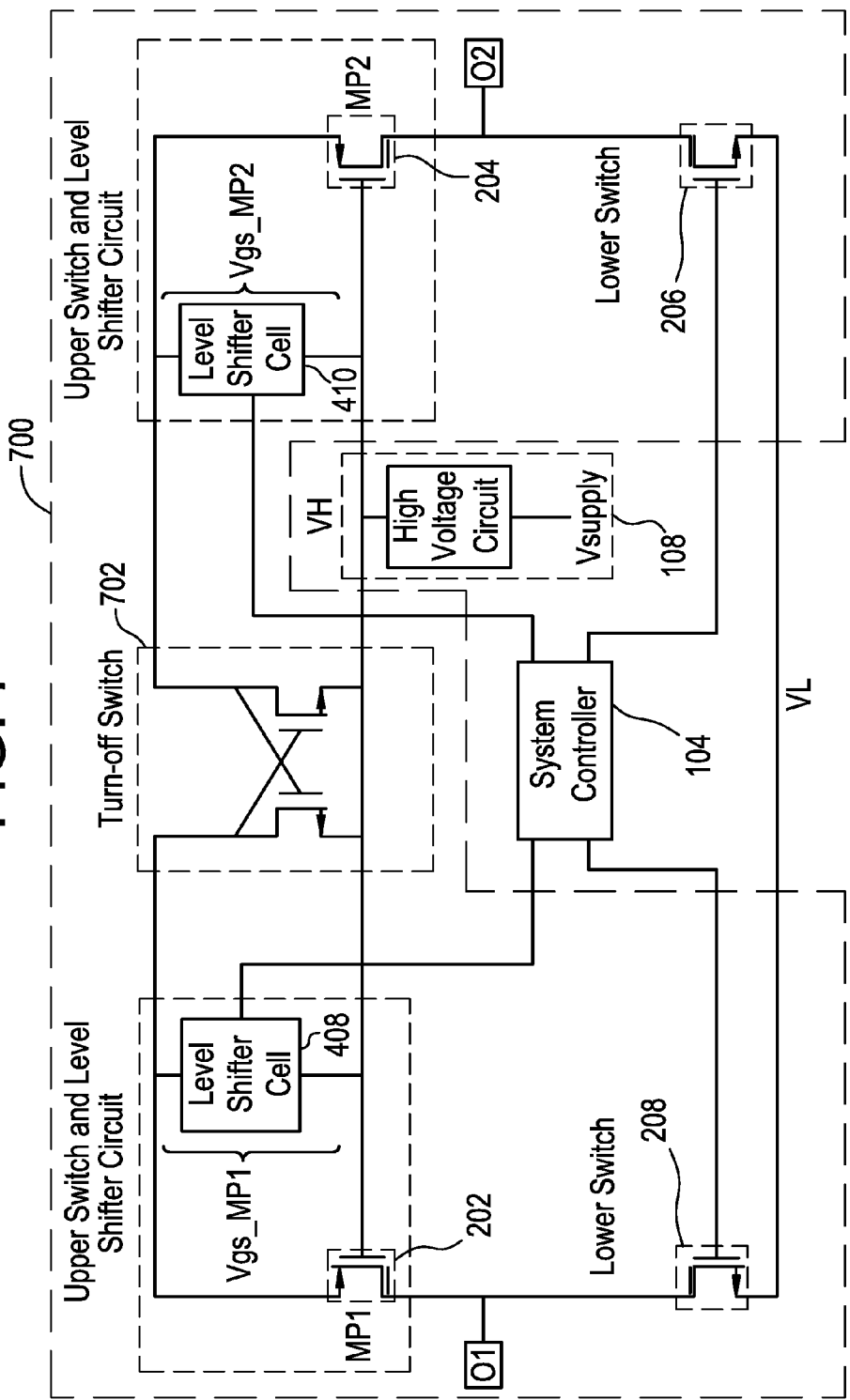
FIG. 7 is a diagrammatic representation of a second exemplary H-bridge/H-bridge controller circuit in accordance with the present invention.

Referring now to FIG. 7, there is illustrated a diagrammatic representation of a second exemplary embodiment of an H-bridge/H-bridge controller circuit 700 in accordance with the present invention. Also illustrated in FIG. 7 are the system controller 104 and the lens power supply 108 which is connected in a manner different from that with respect to the first exemplary embodiment. The level shifter cells 408 and 410 are the same as those described above with respect to FIGS. 4-6, but the connection is different and thus its operation is different. More specifically, the lens power supply 108 supplies VH to both gates of the PMOS switches 202 and 204, and the level shifter cells 408 and 410 create the vgs_MP1 and vgs_MP2 voltages by raising the source voltages of their respective PMOS switches 202 and 204. This is different from the first exemplary embodiment in that, in the first exemplary embodiment the source is held at VH level and lowers the gate voltages utilizing the level shifter cells 408 and 410. This second exemplary embodiment includes a turn-off switch circuit 702 that is less complex than that of the first exemplary embodiment and does not require an additional level shifter cell to turn it off. A disadvantage over the first exemplary embodiment is that the charge provided to the load is limited to the amount provided by the individual level shifter cells 408 and 410 in the H-bridge control circuit and not the reservoir capacitor 506 (see FIG. 5) connected to VH. A detailed description of the turn-off switch circuit 702 is given below with respect to FIG. 8.

Figure 8:
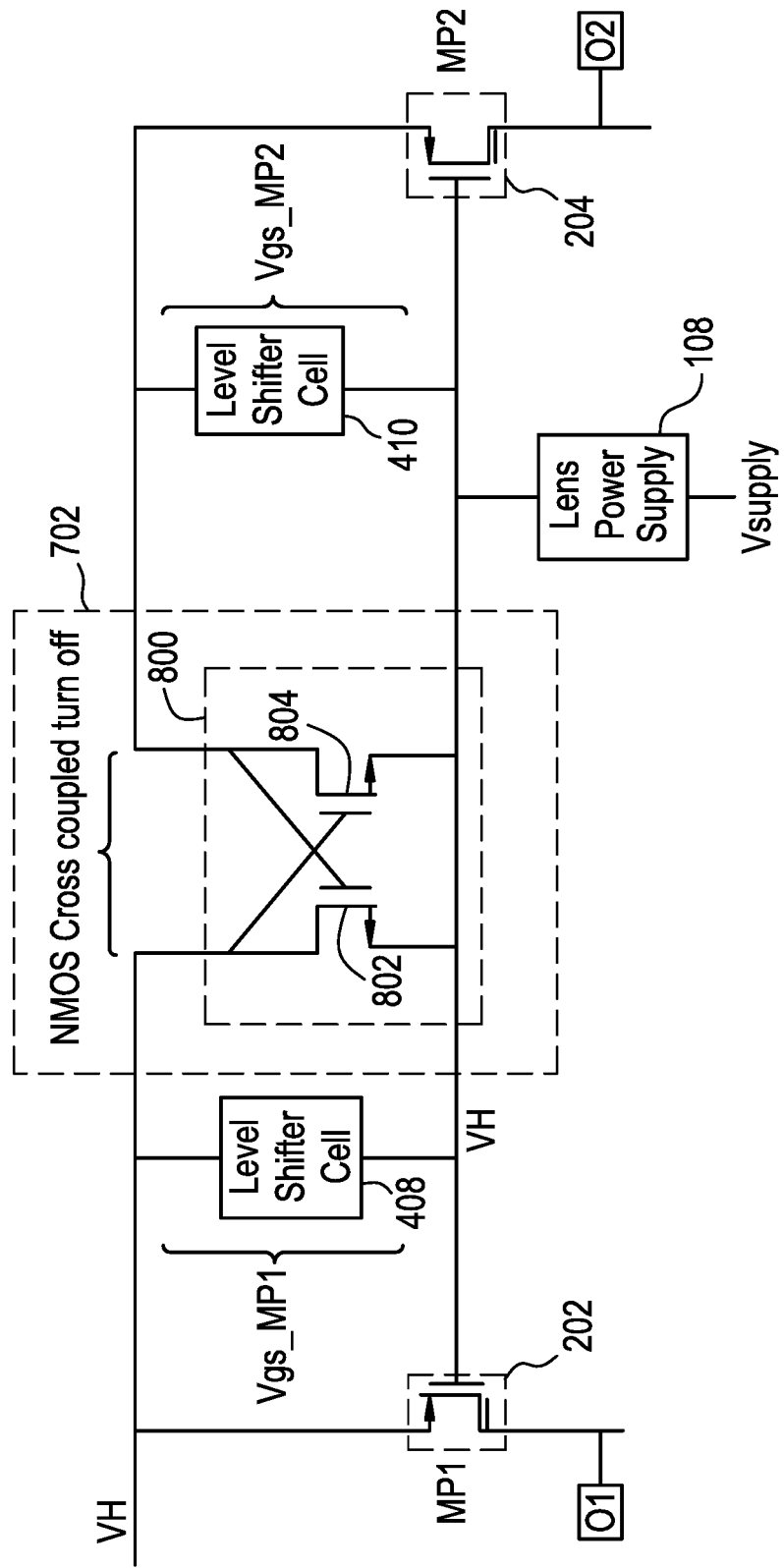
FIG. 8 is a diagrammatic representation of an upper switch and level shifter circuit of the second exemplary H-bridge/H-bridge controller circuit of FIG. 7.

FIG. 8 is a diagrammatic representation of the upper half of the second exemplary embodiment of the H-bridge/H-bridge control circuit 700 of FIG. 7. The main advantage of this configuration is the self-turn-off effect that occurs when, for instance, level shifter cell 408 is deactivated but not fully discharged such that the vgs_MP2 is not zero. Any loading on O2 creates a demand on the PMOS switch 204 to supply current thru the drain which is supplied by the source. Since, there is no longer a supply via the level shifter cell 410 present at the source of PMOS switch 204 except the residual vgs_MP2 voltage, thus the source is pulled lower towards the gate and drain. The vgs_MP2 is reduced to zero volts and thus shuts off PMOS switch 204. The PMOS switch 202 side works in a similar fashion where as any loads on O1 that pull current out of this node will pull the source of PMOS switch 202 toward its gate and drain, and will collapse the vgs_MP1 voltage to zero voltage and thus turn itself off. In addition, there is a NMOS cross-coupled circuit 800, comprising NMOS transistors 802 and 804, to assist in deactivating the opposite level shifter cell. If level shifter cell 408 is off, but vgs_MP1 is not completely at a zero voltage, activating level shifter cell 410 will create sufficient voltage, VC, across the gate to source voltage of NMOS transistor 802 to activate NMOS transistor 804 and thus the level shifter cell 408 and bring vgs_MP1 to zero voltage and shut it off completely. The opposite also works, if vgs_MP2 is not zero volts and level shifter cell 408 is activated, vgs_MP1 is created and sufficient to activate NMOS transistor 804 to short out vgs_MP2 and completely turn off PMOS switch 204.

The level shifter cell comprises buffers, capacitors and a charge pump. The buffers drive the capacitors, which level-shift between the VL and VH voltage levels and provide charge to the charge pump, which in turn creates the VC voltage to activate the appropriate switch. The only active current is through these capacitors where on each clock cycle charge is added and removed from the charge pump circuitry connected on the VH bus such that the net change during steady-state is about zero, thus looking like a high impedance to the VH supply. Little or no current draw from the VH supply is an important requirement of the circuitry. In addition, no other power supplies are required, the start-up does not suffer from latch up or ramping issues, and it is fairly simple.

Figure 9:
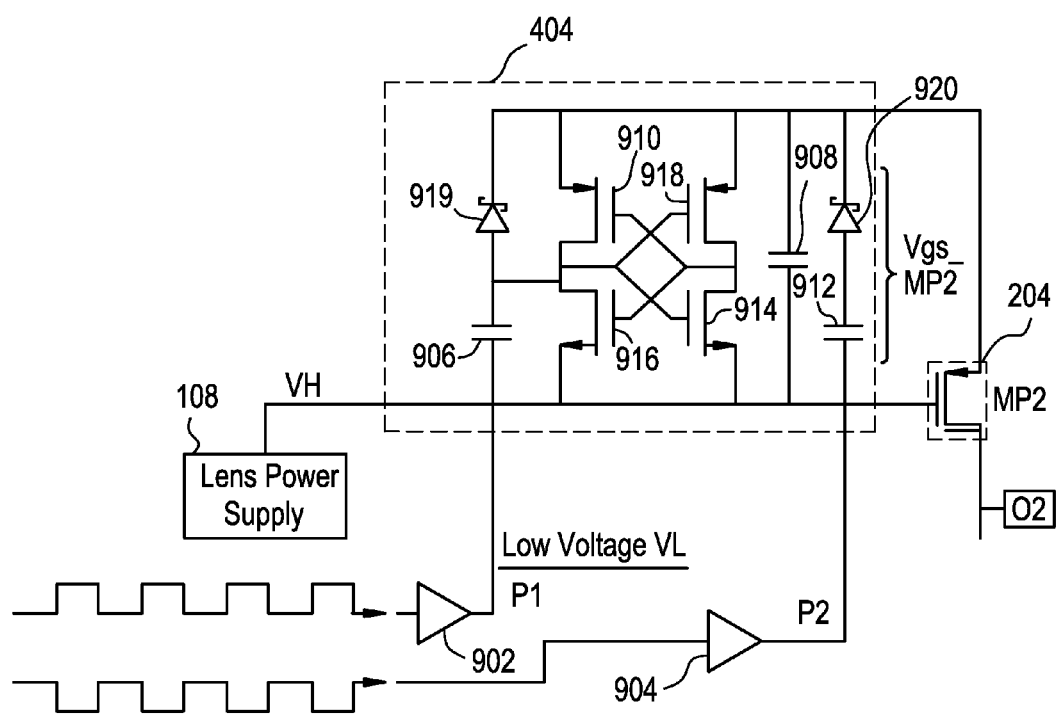
FIG. 9 is a diagrammatic representation of the turn-off switch circuit of the second exemplary H-bridge/H-bridge controller circuit of FIG. 4.

Different types of charge pump cells may be utilized in accordance with the present invention; however, the exemplary one is a cross-coupled charge pump cell where there are two capacitors driving the cell and the cell will create the VC across PMOS switch 202 or PMOS switch 204, as shown in FIG. 9 as upper switch and charge pump 404 shown for PMOS switch 204 control, but equally applicable to PMOS switch 202 control. The control voltage, VC, is equal to about VL, thus it provides a safe and effective VC voltage to the control the switches.

Referring to FIG. 9, the driver buffers 902 and 904 create a square wave output at P1 oscillating between VL and GND in magnitude and the output P2 which is 180 degrees out of the phase of P1. When P1 is going from low to high, the charge from capacitor 906 is transferred to capacitor 908 via an active PMOS transistor 910, thus adding the charge to capacitor 908. PMOS transistor 910 is activated because capacitor 912 is going low and pulling the gate of the PMOS transistor 910 low. Simultaneously, P2 is going high to low causing capacitor 912 to pull charge from VH thru a now active NMOS transistor 914. NMOS transistor 914 is activated because capacitor 906 raised the gate voltage of NMOS transistor 914. When P1 is going from high to low, the charge from capacitor 906 is removed from VH thru an active NMOS transistor 916. Again, simultaneously, P2 is going low to high causing capacitor 912 to charge capacitor 908 though an active PMOS transistor 918 to charge up capacitor 908.

This process causes the capacitor 908 to increase in charge, though several cycles, to the required vgs_MP2 voltage. Because the charge pump drives the source, it acts to raise the output voltage by about VL above the VH supply. It also supplies the charge for that is transferred to the load O2 as needed. Furthermore, when P1 is going low to high, capacitor 906 charges up capacitor 908 through an active PMOS transistor 910 and simultaneously P2 is going high to low and is removing charge from VH, thus the net charge to the high voltage circuitry is zero, or close to it, thus it fulfills the requirement to have no or little loading on the VH circuitry.

During the opposite cycle, where P2 goes low to high, the charge from capacitor 912 is transferred to capacitor 908 via an active PMOS transistor 918, thus providing charge to create the vgs_MP2. Simultaneously, P1 is going high to low causing capacitor 906 to pull charge from VH thru a now active NMOS transistor 916. Again the charge added and the charge taken away from the high voltage node VH is about the same, thus looking like a very high impedance.

Schottky diodes 919 and 920 are used to suppress the unwanted effects of the parasitic PNP device from between the drain (P), body (N), and substrate (P) in the PMOS devices 901 and 908. During the initial charging, the drain can be at higher potential than the body, thus activating this parasitic PNP which will significantly load the circuit with a shunt path back to ground (substrate). The diodes 519 and 520 act to shunt the drain to body junction of the parasitic PNP because the forward voltage is lower, thus preventing the parasitic PNP from activating.

Figure 10:
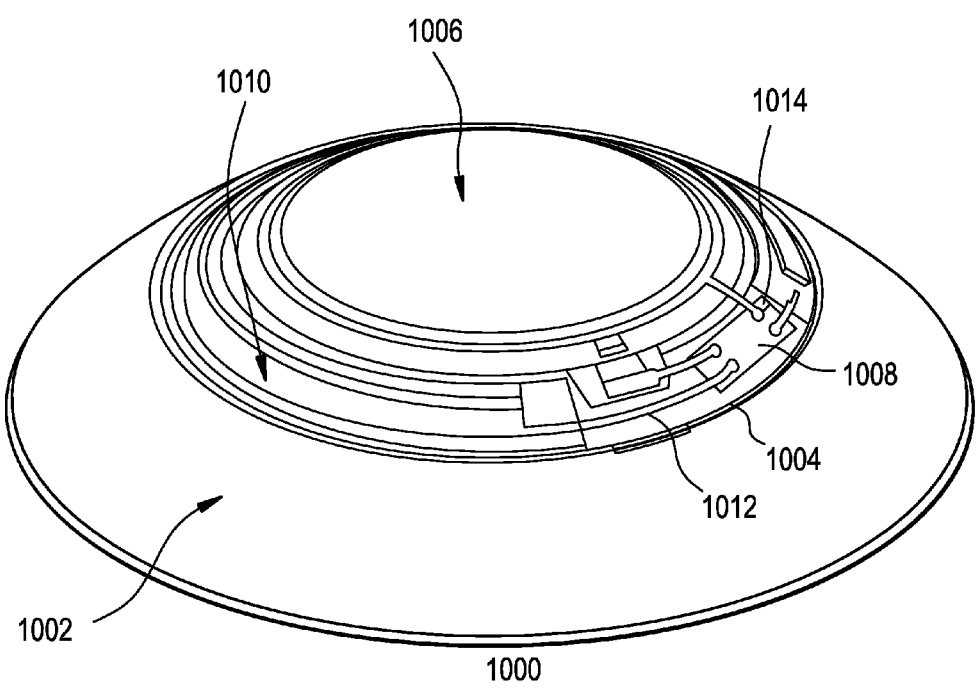
FIG. 10 is a diagrammatic representation of an exemplary electronic insert, including a lens driver, for a powered contact lens in accordance with the present invention.

Referring now to FIG. 10, there is illustrated an exemplary contact lens with an electronic insert comprising the lens driver in accordance with exemplary embodiments of the present invention. The exemplary contact lens 1000 comprises a soft plastic portion 1002 which comprises an electronic insert 1004. This electronic insert 1004 includes a lens 1006 which is activated or controlled by the electronics described herein, for example, focusing near or far depending up activation. Circuitry 1008 mounts onto the insert 1004 and is connected to a power source 1010, such as batteries via one or more electrical interconnect traces 1012. Additional circuitry may also be connected via the electrical interconnect traces 1012. Circuitry 1008 may include any of the components set forth herein, including one or more sensors 1014.

Those of ordinary skill in the art will recognize that further embodiments and variations of the variable-focus lens system are possible. The input to the voltage multiplier may be coupled directly to the power source or it may be coupled to the output of a voltage regulator. The system may comprise an H-bridge to provide flexible control of the lens terminal voltages, half of an H-bridge with only one set of PMOS and NMOS switches, a simple switch to one terminal with the other terminal grounded, or no switches with the lens always coupled in one way to the voltage multiplier output. Each variation may provide a different tradeoff between system cost, area and performance or efficiency.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin-film technology and/or transparent materials. Transparent materials may be utilized as the technology becomes available. If these technologies are utilized, the electronic components may be placed in any suitable location as long as they are compatible with the optics.

It is important to note that the circuitry described herein may be implemented in hardware, software or a combination of hardware and software. In addition, the circuit board utilized herein may comprise any suitable substrate, including copper traces on a flexible polyimide substrate with a nickel-gold surface finish.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic apparatus comprising:
an ophthalmic lens for use in at least one of in or on the eye;
an optic element incorporated into the ophthalmic lens, the optic element configured for at least one of vision correction and vision enhancement and having one or more of electronically controlled focal length, electronically controlled light transmission, and electronically controlled polarization; and
an electronic system incorporated into the ophthalmic lens, the electronic system including:
a power source;
an H-bridge circuit configured to control a voltage supplied to the optic element, to reverse the polarity of a voltage supplied to the optic element and to short the optic element, the H-bridge circuit including first and second lower switches implemented as N-channel MOSFET transistors, and first and second upper P-channel MOSFET switches;
an H-bridge control circuit used to control the first and second upper P-channel MOSFET switches using level shifter cells and configured to be a high-impedance circuit thereby preventing a loading of the power source, the level shifter cells comprising buffers, a capacitor coupling circuit, and a charge pump cell, wherein the capacitors level shift between a low voltage and a high voltage and transfer the charge to the charge pump cell, the charge pump cell provides an activation voltage for the first and second upper P-channel MOSFET switches, and an active turn-off circuit comprising control switches designed to deactivate the first and second upper P-channel MOSFET switches as necessary by activating an additional level shifter circuit to activate the control switches, and a cross-coupled switch circuit between the outputs of the two level shifter cells thereby ensuring only one of the first and second upper P-channel MOSFET switches is on at a time; and a system controller configured to provide control and timing signals for the electronic system, wherein the power source provides a voltage to sources of the first and second upper P-channel MOSFET transistor and to the H-Bridge control circuit.

2. The ophthalmic apparatus according to claim 1, wherein the ophthalmic device comprises a contact lens.

3. The ophthalmic apparatus according to claim 2, wherein the contact lens comprises a soft contact lens.

4. The ophthalmic apparatus according to claim 2, wherein the contact lens comprises a hybrid soft/rigid contact lens.

5. The ophthalmic apparatus according to claim 1, wherein the ophthalmic device comprises an intraocular lens.

6. The ophthalmic apparatus according to claim 1, wherein the optic element operates in at least two focal lengths.

7. The ophthalmic apparatus according to claim 1, wherein the electronic system is implemented on an integrated circuit.

8. The ophthalmic apparatus according to claim 1, wherein the optic element comprises a liquid meniscus lens.

9. The ophthalmic apparatus according to claim 1, wherein the optic element comprises a liquid crystal lens.

10. The ophthalmic apparatus according to claim 1, wherein the power source comprises a battery.

11. The ophthalmic apparatus according to claim 7, wherein the integrated circuit is incorporated onto a circuit board.

12. The ophthalmic apparatus according to claim 11, wherein the circuit board is configured as an annular ring.

13. The ophthalmic apparatus according to claim 12, wherein the annular ring is formed into a conical section for incorporation into a contact lens.

14. The ophthalmic apparatus according to claim 12, wherein the annular ring is formed into a conical section for incorporation into an intraocular lens.

15. The ophthalmic apparatus according to claim 1, wherein the optic element operates in at least two states of light transmission.

16. The ophthalmic apparatus according to claim 1, wherein the optic element operates in at least two states of light polarization.

17. An ophthalmic apparatus comprising:
an ophthalmic lens for use in at least one of in or on the eye;
an optic element incorporated into the ophthalmic lens, the optic element configured for at least one of vision correction and vision enhancement and having one or more of electronically controlled focal length, electronically controlled light transmission, and electronically controlled polarization; and
an electronic system incorporated into the ophthalmic lens, the electronic system including:
a power source;
an H-bridge circuit configured to control a voltage supplied to the optic element, to reverse the polarity of a voltage supplied to the optic element and to short the optic element, the H-bridge circuit including first and second lower switches implemented as N-channel MOSFET transistors, and first and second upper P-channel MOSFET switches;

an H-bridge control circuit used to control the first and second upper P-channel MOSFET switches using level shifter cells and configured to be a high-impedance circuit thereby preventing a loading of the power source, the level shifter cells comprising buffers, a capacitor coupling circuit, and a charge pump cell, wherein the capacitors level shift between a low voltage and a high voltage and transfer the charge to the charge pump cell, the charge pump cell provides an activation voltage for the first and second upper P-channel MOSFET switches, and an active turn-off circuit comprising control switches designed to deactivate the first and second upper P-channel MOSFET switches as necessary by activating a cross-coupled switch circuit between the outputs of the two level shifter cells thereby ensuring only one of the first and second upper P-channel MOSFET switches is on at a time; and a system controller configured to provide control and timing signals for the electronic system, wherein the power source provides a voltage to gates of the first and second upper P-channel MOSFET transistor and to the H-Bridge control circuit.

18. The ophthalmic apparatus according to claim 17, wherein the ophthalmic device comprises a contact lens.

19. The ophthalmic apparatus according to claim 18, wherein the contact lens comprises a soft contact lens.

20. The ophthalmic apparatus according to claim 18, wherein the contact lens comprises a hybrid soft/rigid contact lens.

21. The ophthalmic apparatus according to claim 17, wherein the ophthalmic device comprises an intraocular lens.

22. The ophthalmic apparatus according to claim 17, wherein the optic element operates in at least two focal lengths.

23. The ophthalmic apparatus according to claim 17, wherein the electronic system is implemented on an integrated circuit.

24. The ophthalmic apparatus according to claim 17, wherein the optic element comprises a liquid meniscus lens.

25. The ophthalmic apparatus according to claim 17, wherein the optic element comprises a liquid crystal lens.

26. The ophthalmic apparatus according to claim 17, wherein the power source comprises a battery.

27. The ophthalmic apparatus according to claim 23, wherein the integrated circuit is incorporated onto a circuit board.

28. The ophthalmic apparatus according to claim 27, wherein the circuit board is configured as an annular ring.

29. The ophthalmic apparatus according to claim 28, wherein the annular ring is formed into a conical section for incorporation into a contact lens.

30. The ophthalmic apparatus according to claim 28, wherein the annular ring is formed into a conical section for incorporation into an intraocular lens.

* * * * *